United States Patent
Neckers et al.

(10) Patent No.: US 9,517,224 B2
(45) Date of Patent: Dec. 13, 2016

(54) METHODS OF TREATING PATIENTS INFECTED WITH HIV AND HTLV

(71) Applicant: THE UNITED STATES OF AMERICA, AS REPRESENTED BY THE SECRETARY, DEPARTMENT OF HEALTH AND HUMAN SERVICES, Washington, DC (US)

(72) Inventors: Leonard M. Neckers, Bethesda, MD (US); Carole Sourbier, Rockville, MD (US); Jane B. Neckers, Bethesda, MD (US); Min-Jung Lee, North Potomac, MD (US); John A. Beutler, Union Bridge, MD (US); W. Marston Linehan, North Bethesda, MD (US); Bradley T. Scroggins, Rockville, MD (US); Sunmin Lee, Boyds, MD (US)

(73) Assignee: The United States of America as represented by the Secretary, Department of Health and Human Services, Washington, DC (US)

(*) Notice: Subject to any disclaimer, the term of this patent is extended or adjusted under 35 U.S.C. 154(b) by 0 days.

(21) Appl. No.: 14/442,865

(22) PCT Filed: Nov. 13, 2013

(86) PCT No.: PCT/US2013/069796
§ 371 (c)(1),
(2) Date: May 14, 2015

(87) PCT Pub. No.: WO2014/078350
PCT Pub. Date: May 22, 2014

(65) Prior Publication Data
US 2015/0283111 A1    Oct. 8, 2015

Related U.S. Application Data

(60) Provisional application No. 61/726,975, filed on Nov. 15, 2012.

(51) Int. Cl.
*A61K 31/55* (2006.01)
*A61K 31/35* (2006.01)
(Continued)

(52) U.S. Cl.
CPC ............. *A61K 31/35* (2013.01); *A61K 31/352* (2013.01); *A61K 45/06* (2013.01)

(58) Field of Classification Search
CPC .................................................. A61K 31/352
(Continued)

(56) References Cited

U.S. PATENT DOCUMENTS 7,772,197 B2    8/2010   Daifuku et al.
8,410,292 B2 *  4/2013   Beutler et al. ....... C07D 493/08
                                                        540/581
(Continued)

FOREIGN PATENT DOCUMENTS

EP    1 749 830 A1    2/2007
EP    1749830 A1 *    7/2007
(Continued)

OTHER PUBLICATIONS

Ratnayake et al. "Englerin A, a Selective inhibitor of Renal Cancer cell growth, from Phyllanthus engleri," Organic Letters, 2008, vol. 11, No. 1, pp. 57-60.*
(Continued)

*Primary Examiner* — Shengjun Wang
(74) *Attorney, Agent, or Firm* — Leydig, Voit & Mayer, Ltd.

(57) ABSTRACT

Disclosed is a method of activating protein kinase C theta (PKCθ) in an HIV or HTLV infected animal comprising administering to the animal an effective amount of a compound of formula (I): Formula (I), or an epimer thereof; wherein Ar and $R^1$-$R^6$ are described herein. Examples of (Continued)

diseases or conditions associated with PKCθ include HIV1 infection, AIDS, HTLV infection, and adult T cell leukemia/lymphoma.

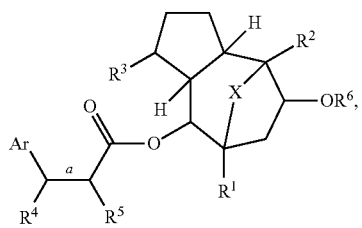

(I)

20 Claims, 1 Drawing Sheet (51) Int. Cl.
*A61K 45/06* (2006.01)
*A61K 31/352* (2006.01)

(58) Field of Classification Search
USPC .......................................................... 514/455
See application file for complete search history.

(56) References Cited

U.S. PATENT DOCUMENTS

| | | | |
|---|---|---|---|
| 9,101,601 | B2 | 8/2015 | Neckers et al. |
| 2003/0186941 | A1 | 10/2003 | Roberts et al. |
| 2007/0155681 | A1 | 7/2007 | Shapiro et al. |
| 2008/0226589 | A1 | 9/2008 | Han |
| 2010/0168004 | A1 | 7/2010 | Williams et al. |
| 2010/0286259 | A1 | 11/2010 | Beutler et al. |
| 2010/0291067 | A1 | 11/2010 | Planelles et al. |
| 2011/0014699 | A1 | 1/2011 | Wender et al. |
| 2011/0112073 | A1 | 5/2011 | Thiele et al. |

FOREIGN PATENT DOCUMENTS

| | | |
|---|---|---|
| WO | WO 00/56341 A1 | 9/2000 |
| WO | WO 2009/088854 A1 * | 7/2009 |
| WO | WO 2011/073739 A1 | 6/2011 |
| WO | WO 2011/120886 A1 | 10/2011 |
| WO | WO 2012/035321 A1 | 3/2012 |
| WO | WO 2013/106226 A2 | 7/2013 |

OTHER PUBLICATIONS

Chan et al. "Chemical Synthesis and Biological Evaluation of the Englerin Analogues," CHEMMEDCHEM, Jan. 2011, vol. 6, No. 3, 420-423.*
Bazarbachi et al., "Meta-analysis on the use of zidovudine and interferon-alfa in adult T-cell leukemia/lymphoma showing improved survival in the leukemic subtypes," *J. Clin. Oncol.*, 28 (27), 4177-4183 (2010).
Folks et al., "Characterization of a promonocyte clone chronically infected with HIV and inducible by 13-phorbol-12-myristate acetate," *J. Immunol.*, 140 (4), 1117-1122 (1988).
International Preliminary Report on Patentability, Application No. PCT/US2013/069796, date issued May 19, 2015.
International Search Report, Application No. PCT/US2013/069796, date mailed Feb. 17, 2014.
Kavanagh et al., "Restoring HSP70 deficiencies improves glucose tolerance in diabetic monkeys," *Am. J. Physiol. Endocrinol. Metab.*, 300 (5), E894-E901 (2011).
Manel et al., "The ubiquitous glucose transporter GLUT-1 is a receptor for HTLV," *Cell*, 115 (4), 449-459 (2003).
Ratnayake et al., "Englerin A, a selective inhibitor of renal cancer cell growth, from *Phyllanthus engleri.*," *Org. Lett.*, 11 (1), 57-60 (2009).
Rawat et al., "Cellular heat shock factor 1 positively regulates human immunodeficiency virus-1 gene expression and replication by two distinct pathways," *Nucleic Acids Res.*, 39 (14), 5879-5892 (2011).
Smith et al., "The HIV Nef protein associates with protein kinase C theta," *J. Biol. Chem.*, 271 (28), 16753-16757 (1996).
Williams et al., "Prostratin antagonizes HIV latency by activating NF-κB," *J. Biol. Chem.*, 279 (40), 42008-42017 (2004).
Written Opinion of the International Searching Authority, Application No. PCT/US2013/069796, date mailed Feb. 17, 2014.

* cited by examiner

METHODS OF TREATING PATIENTS INFECTED WITH HIV AND HTLV

CROSS-REFERENCE TO A RELATED APPLICATION

This application is a U.S. National Phase of International Patent Application No. PCT/US2013/069796, filed Nov. 13, 2013, which claims the benefit of U.S. Provisional Patent Application No. 61/726,975, filed Nov. 15, 2012, the disclosures of which are incorporated herein by reference.

BACKGROUND OF THE INVENTION

The human immunodeficiency virus-1 (HIV1) affects 1.4 million patients in the US and over 33 million worldwide. The human and monetary costs of this disease compel the development of new therapies leading to a cure. The long half-life of latent reservoirs of HIV1-infected cells is the main barrier for virus eradication. One current therapeutic strategy is to activate latent reservoirs of HIV1-infected cells while treating them with Highly Active Antiretroviral Therapy (HAART). PKC activators (phorbol esters) or interleukins (IL-2, IL-7) are examples of agents used for this purpose. However, the high toxicity and poor efficacy of these agents has impeded their development in the clinic. The foregoing shows that there is an unmet need for activating latent reservoirs of HIV-infected cells.

The human T cell lymphotropic virus (HTLV) is associated with Adult Tcell leukemia/lymphoma (ATL), a very aggressive malignancy. HTLV patients with acute subtypes of ATL have a poor prognosis due, in part, to chemotherapy resistance, and to immune deficiency leading to the development of opportunist diseases. The foregoing shows that there is an unmet need for therapeutic agents for treating or improving the survival of ATL patients.

BRIEF SUMMARY OF THE INVENTION

In an embodiment, the present invention provides a method of treating an HIV-infected animal comprising co-administering to the animal (i) an effective amount of a compound of formula (I):

(I)

or an epimer thereof; wherein

Ar is an aryl group, optionally substituted with one or more substituents selected from the group consisting of $C_1$-$C_6$ alkyl, $C_1$-$C_6$ hydroxyalkyl, $C_1$-$C_6$ alkoxy, halo, and nitro;

X is O, NH, or S;

$R^2$ and $R^3$ are independently $C_1$-$C_6$ alkyl;

$R^1$ is isopropyl or isopropenyl;

"a" is a single bond or a double bond;

when "a" is a double bond, $R^4$ is hydrogen, and $R^5$ is halo or H;

when "a" is a single bond, $R^4$ is selected from the group consisting of halo, hydroxy, and $C_1$-$C_6$ alkoxy and $R^5$ is halo or H; and $R^6$ is H, $C_1$-$C_6$ alkyl carbonyl, or hydroxy $C_1$-$C_6$ alkyl carbonyl, and (ii) at least one antiviral agent.

In another embodiment, the present invention provides a method of treating an HTLV-infected animal comprising co-administering to the animal (i) an effective amount of a compound of formula (I) and (ii) at least one antiviral agent.

In another embodiment, the present invention provides a method of increasing the activity of latent infected CD4+ cells of an animal carrying HIV comprising administering to the animal an effective amount of a compound of formula (I).

In another embodiment, the present invention provides a method of inhibiting Treg activation and number in an animal carrying HTLV comprising administering to the animal an effective amount of a compound of formula (I).

In another embodiment, the present invention provides a method of decreasing Glut1 expression in an ATL cell in an animal carrying HTLV comprising administering to the animal an effective amount of a compound of formula (I).

The invention provides methods for using englerin A and other epoxy-guaine derivatives as an adjuvant therapy for HIV1-infected patients, patients having AIDS, patients having ATL, and other immunodeficient patients carrying viral infection.

DETAILED DESCRIPTION OF THE INVENTION

The present invention is predicated, at least in part, on the surprising discovery that englerin A, a compound for use in an embodiment of the invention, has the ability to selectively activate PKCθ. PKCθ is selectively expressed in tumors and in immune cells (e.g., T cells). It was observed that englerin A induces NFκB and HSF1 transcriptional activities in a PKCθ-dependent manner in activated T cells, and enhances PKCθ interaction with the HIV protein Nef. In activated T cells, HIV1 viral replication is induced by PKCθ via phosphorylation of Nef and by the activation of the transcription factors NFκB and HSF1 from the host cell. It was further observed that englerin A treatment of the blood of ATL patients showed a significant decrease in Treg markers in 1 out of 3 patients, suggesting that T cells are activated. It was further observed that englerin A inhibits Glut1 protein expression. Both HTLV-1 and HTLV-2 glycoproteins interact with and use the glucose transporter Glut1 as a receptor to infect naive cells.

Taken together, the above data demonstrates that englerin A activates signaling pathways that are usually weakened in latent reservoirs of HIV1-infected cells in vitro. The data also suggests that englerin A may sensitize HIV1-infected patients to HAART by selectively activating viral replication in T cells, and with potentially limited toxicity due to the selectivity of EA towards PKCθ.

It has also been discovered that englerin A treatment of the blood of adult T cell leukemia/lymphoma (ATL) patients showed a significant increase in Treg markers in 1 out of 3 patients, suggesting that T cells are activated. In addition, both human T cell lymphotropic viruses HTLV-1 and HTLV-2 glycoproteins interact with and use the glucose transporter Glut1 as a receptor to infect naïve cells. It has been shown that englerin A inhibits Glut1 protein expression. Thus, englerin A will activate and sensitize T cells to anti-viral therapy in patients with ATL without increasing the cell to cell neo-infection of CD4+ T cells with the virus.

Thus, englerin A and other epoxy-guaine derivatives may be useful as an adjuvant therapy for HIV1-infected patients, patients having AIDS, patients having ATL, and other immunodeficient patients with viral infections.

Accordingly, in accordance with an embodiment, the invention provides a method of activating protein kinase C theta (PKCθ) in an HIV or HTLV infected animal comprising administering to the animal an effective amount of a compound of formula (I):

(I)

or an epimer thereof; wherein

Ar is an aryl group, optionally substituted with one or more substituents selected from the group consisting of $C_1$-$C_6$ alkyl, $C_1$-$C_6$ hydroxyalkyl, $C_1$-$C_6$ alkoxy, halo, and nitro;

X is O, NH, or S;

$R^2$ and $R^3$ are independently $C_1$-$C_6$ alkyl;

$R^1$ is isopropyl or isopropenyl;

"a" is a single bond or a double bond;

when "a" is a double bond, $R^4$ is hydrogen, and $R^5$ is halo or H;

when "a" is a single bond, $R^4$ is selected from the group consisting of halo, hydroxy, and $C_1$-$C_6$ alkoxy and $R^5$ is halo or H; and $R^6$ is H, $C_1$-$C_6$ alkyl carbonyl, or hydroxy $C_1$-$C_6$ alkyl carbonyl.

In an embodiment, the invention provides a compound formula (I):

(I)

or an epimer thereof; wherein

Ar is an aryl group, optionally substituted with one or more substituents selected from the group consisting of $C_1$-$C_6$ alkyl, $C_1$-$C_6$ hydroxyalkyl, $C_1$-$C_6$ alkoxy, halo, and nitro;

X is O, NH, or S;

$R^2$ and $R^3$ are independently $C_1$-$C_6$ alkyl;

$R^1$ is isopropyl or isopropenyl;

"a" is a single bond or a double bond;

when "a" is a double bond, $R^4$ is hydrogen, and $R^5$ is halo or H;

when "a" is a single bond, $R^4$ is selected from the group consisting of halo, hydroxy, and $C_1$-$C_6$ alkoxy and $R^5$ is halo or H; and $R^6$ is H, $C_1$-$C_6$ alkyl carbonyl, or hydroxy $C_1$-$C_6$ alkyl carbonyl;

for use in activating protein kinase C theta (PKCθ) in an HIV or HTLV infected animal in need thereof In accordance with any of the embodiments of the invention, the term "aryl" refers to a mono, bi, or tricyclic carbocyclic ring system having one, two, or three aromatic rings, for example, phenyl, naphthyl, anthracenyl, or biphenyl. The term "aryl" also refers to an unsubstituted or substituted aromatic carbocyclic moiety, as commonly understood in the art, and includes monocyclic and polycyclic aromatics such as, for example, phenyl, biphenyl, naphthyl, anthracenyl, pyrenyl, and the like. An aryl moiety generally contains from, for example, 6 to 30 carbon atoms, preferably from 6 to 18 carbon atoms, more preferably from 6 to 14 carbon atoms and most preferably from 6 to 10 carbon atoms. It is understood that the term aryl includes carbocyclic moieties that are planar and comprise 4n+2π electrons, according to Hückel's Rule, wherein n=1, 2, or 3.

Whenever a range of the number of atoms in a structure is indicated (e.g., a $C_{1-6}$ or $C_{1-4}$ alkyl, alkoxy, hydroxyalkyl, etc.), it is specifically contemplated that any sub-range or individual number of carbon atoms falling within the indicated range also can be used. Thus, for instance, the recitation of a range of 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, and/or 6 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 2-3 carbon atoms, 2-4 carbon atoms, 2-5 carbon atoms, 2-6 carbon atoms, 3-4 carbon atoms, 3-5 carbon atoms, 3-6 carbon atoms, 4-5 carbon atoms, and 4-6 carbon atoms, as appropriate).

In any of the above embodiments of the invention, $R^6$ is hydroxy $C_1$-$C_6$ alkyl carbonyl, particularly $C_1$-$C_3$ hydroxyalkyl carbonyl, and more particularly hydroxymethyl carbonyl.

In accordance with any of the embodiments, $R^5$ is halo, i.e., fluoro, chloro, bromo, or iodo, particularly chloro.

In any of the embodiments of the invention, Ar is phenyl, naphthyl, or anthracenyl, optionally substituted with $C_1$-$C_6$ alkyl, $C_1$-$C_6$ hydroxyalkyl, $C_1$-$C_6$ alkoxy, halo, or nitro. In a particular embodiment, Ar is phenyl, optionally substituted with $C_1$-$C_6$ alkyl, $C_1$-$C_6$ hydroxyalkyl, $C_1$-$C_6$ alkoxy, halo, or nitro.

In any of the embodiments of the invention, X is preferably O.

In any of the embodiments of the invention, $R^1$ is particularly isopropyl.

In any of the embodiments of the invention, "a" is a double bond or single bond. When "a" is a double bond, the double bond can be E, Z, or a mixture of E and Z (i.e., E/Z). In embodiments where "a" is a single bond, $R^4$ is hydroxy, chloro, or ethoxy.

In another embodiment, the invention provides methods wherein, in the compound of formula (I) or epimer thereof, $R^6$ is $C_1$-$C_6$ alkylcarbonyl, particularly, $C_1$-$C_3$ alkylcarbonyl.

In any of the embodiments, in the compound of formula (I) or epimer thereof, $R^2$ and $R^3$ are particularly methyl.

Specific examples of the compound of formula (I) for use in any of the above embodiments are:

2'-Chloroenglerin A,

2'-Chloro,3'-hydroxydihydroenglerin A (epimer 1, 2, 3, or 4),

2',3'-Dichlorodihydroenglerin A (epimer 1 or 2), or

2'-Chloro,3'-ethoxydihydroenglerin A,
wherein the double bond "a" in 2'-Chloroenglerin A can be E, Z, or a mixture of E and Z. 2'-chloro,3'-hydroxydihydroenglerin A (epimers 1-4) have the same planar structure but are epimers of one another. 2',3'-dichlorodihydroenglerin A (epimers 1 and 2) have the same planar structure but are epimers of each other.

In a specific embodiment of the above methods, the compound of formula (I) is englerin A, which is of the formula:

and more specifically, (−)-englerin A:

The compounds above can be isolated or purified from natural sources, for example, from the root bark and stem bark of the plant *Phyllanthus engleri* Pax (Euphorbiaceae). This species has a long history as a toxic plant. The book "Common Poisonous Plants of East Africa" (B. Verdcourt & E. C. Trump, 1969) reports that the root and bark of this plant are toxic and lethal when smoked. This property has been used for committing suicide. Experimental work has found that the ethanolic extract is toxic to rabbits by oral and intravenous routes. The bark and root are toxic to sheep and cattle. The poisonous principles were not identified.

The above compounds can be isolated from the plant by any suitable method, for example, by solvent extraction and chromatography, as illustrated in the Examples. In accordance with an embodiment of the invention, the isolated or purified compound has a purity of at least 50% or more, for example, 60% or more, 70% or more, 80% or more, or 90% or more. For example, the isolated or purified compounds or epimers can have a purity of about 60% to 100%, preferably from about 80% to about 99%, and more preferably from about 90% to 100% by weight.

The compounds of formula I can be prepared by any suitable synthetic methodology. For example, in a hemisynthetic route, various ester groups [Ar—C($R^4$)-a-C($R^5$)—C(=O)—O-] can be placed on the guaiane derivative after hydrolysis of the naturally occurring ester groups. Esterification can be carried out on the hydroxyl group by methods known to those skilled in the art, for example, through the use of an acid chloride or acid anhydride and a suitable base. The desired ester moieties can be prepared from suitable cinnamoyl moieties. Halogenated englerins can be prepared by halogenating the isolated or purified englerins or during the isolation or purification.

Isolation and/or preparation of englerins and derivatives thereof are described in WO 2009/088854 A1 and WO 2011/120886 A1, the disclosures of which are incorporated herein in their entirety. WO '854 also discloses the utility of englerins and derivatives thereof as anticancer agents.

In accordance with an embodiment, the animal is infected with HIV1. In accordance with another embodiment, the animal is afflicted with AIDS. In another embodiment, the animal is afflicted with ATL. In accordance with other embodiments, the animal is afflicted with T lymphocytopenia due to idiopathic CD4+ lymphocytopenia (ICL), immune deficiency condition, leukemia, or chemotherapy, and combinations thereof. In accordance with other embodiments, the animal is infected with feline leukemia virus or feline immunodeficiency virus retroviral infections. In accordance with an embodiment, the animal is infected with the human T-cell lymphotropic virus (HTLV). In accordance with other embodiments, the compound of formula (I) is administered as an adjuvant in combination with anti-viral agents.

The terms "treat," "prevent," "ameliorate," and "inhibit," as well as words stemming therefrom, as used herein, do not necessarily imply 100% or complete treatment, prevention, amelioration, or inhibition. Rather, there are varying degrees of treatment, prevention, amelioration, and inhibition of which one of ordinary skill in the art recognizes as having a potential benefit or therapeutic effect. In this respect, the inventive methods can provide any amount of any level of treatment, prevention, amelioration, or inhibition of the disorder in a mammal. For example, a disorder, including symptoms or conditions thereof, may be reduced by, for example, 100%, 90%, 80%, 70%, 60%, 50%, 40%, 30%, 20%, or 10%. Furthermore, the treatment, prevention, amelioration, or inhibition provided by the inventive method can include treatment, prevention, amelioration, or inhibition of one or more conditions or symptoms of the disorder, e.g., cancer. Also, for purposes herein, "treatment," "prevention," "amelioration," or "inhibition" can encompass delaying the onset of the disorder, or a symptom or condition thereof.

In accordance with the invention, the term "animal" includes a mammal such as, without limitation, the order Rodentia, such as mice, and the order Lagomorpha, such as rabbits. It is preferred that the mammals are from the order Carnivora, including Felines (cats) and Canines (dogs). It is more preferred that the mammals are from the order Artiodactyla, including Bovines (cows) and Swine (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The compound (or epimer thereof) is administered in a dose sufficient to treat the cancer. Such doses are known in the art (see, for example, the *Physicians' Desk Reference* (2004)). The compounds can be administered using techniques such as those described in, for example, Wasserman et al., *Cancer*, 36, pp. 1258-1268 (1975) and *Physicians' Desk Reference*, 58th ed., Thomson PDR (2004).

Suitable doses and dosage regimens can be determined by conventional range-finding techniques known to those of ordinary skill in the art. Generally, treatment is initiated with smaller dosages that are less than the optimum dose of the compound of the present invention. Thereafter, the dosage is increased by small increments until the optimum effect under the circumstances is reached. The present method can involve the administration of about 0.1 μg to about 50 mg of at least one compound of the invention per kg body weight of the individual. For a 70 kg patient, dosages of from about 10 μg to about 200 mg of the compound of the invention would be more commonly used, depending on a patient's physiological response.

By way of example and not intending to limit the invention, the dose of the pharmaceutically active agent(s) described herein for methods of treating or preventing a disease or condition as described above can be about 0.001 to about 1 mg/kg body weight of the subject per day, for example, about 0.001 mg, 0.002 mg, 0.005 mg, 0.010 mg, 0.015 mg, 0.020 mg, 0.025 mg, 0.050 mg, 0.075 mg, 0.1 mg, 0.15 mg, 0.2 mg, 0.25 mg, 0.5 mg, 0.75 mg, or 1 mg/kg body weight per day. The dose of the pharmaceutically active agent(s) described herein for the described methods can be about 1 to about 1000 mg/kg body weight of the subject being treated per day, for example, about 1 mg, 2 mg, 5 mg, 10 mg, 15 mg, 0.020 mg, 25 mg, 50 mg, 75 mg, 100 mg, 150 mg, 200 mg, 250 mg, 500 mg, 750 mg, or 1000 mg/kg body weight per day.

The pharmaceutically acceptable carrier (or excipient) is preferably one that is chemically inert to the compound of the invention and one that has no detrimental side effects or toxicity under the conditions of use. Such pharmaceutically acceptable carriers preferably include saline (e.g., 0.9% saline), Cremophor EL (which is a derivative of castor oil and ethylene oxide available from Sigma Chemical Co., St. Louis, Mo.) (e.g., 5% Cremophor EL/5% ethanol/90% saline, 10% Cremophor EL/90% saline, or 50% Cremophor EL/50% ethanol), propylene glycol (e.g., 40% propylene glycol/10% ethanol/50% water), polyethylene glycol (e.g., 40% PEG 400/60% saline), and alcohol (e.g., 40% ethanol/60% water). A preferred pharmaceutical carrier is polyethylene glycol, such as PEG 400, and particularly a composition comprising 40% PEG 400 and 60% water or saline. The choice of carrier will be determined in part by the particular compound chosen, as well as by the particular method used to administer the composition. Accordingly, there is a wide variety of suitable formulations of the pharmaceutical composition of the present invention.

The following formulations for oral, aerosol, parenteral, subcutaneous, intravenous, intraarterial, intramuscular, interperitoneal, rectal, and vaginal administration are merely exemplary and are in no way limiting. The pharmaceutical compositions can be administered parenterally, e.g., intravenously, intraarterially, subcutaneously, intradermally, intrathecally, or intramuscularly. Thus, the invention provides compositions for parenteral administration that comprise a solution of the compound of the invention dissolved or suspended in an acceptable carrier suitable for parenteral administration, including aqueous and non-aqueous, isotonic sterile injection solutions.

Overall, the requirements for effective pharmaceutical carriers for parenteral compositions are well known to those of ordinary skill in the art. See *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986). Such compositions include solutions containing anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol (for example in topical applications), or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, and synthetic oils. Specific examples of oils useful in such formulations include peanut, soybean, sesame, cottonseed, corn, olive, petrolatum, and mineral oil. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl-β-aminopropionates, and 2-alkyl-imidazoline quaternary ammonium salts, and (e) mixtures thereof The parenteral formulations typically will contain from about 0.5% or less to about 25% or more by weight of a compound of the invention in solution. Preservatives and buffers can be used. In order to minimize or eliminate irritation at the site of injection, such compositions can contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Topical formulations, including those that are useful for transdermal drug release, are well known to those of skill in the art and are suitable in the context of the present invention for application to skin.

Formulations suitable for oral administration can consist of (a) liquid solutions, such as an effective amount of a compound of the invention dissolved in diluents, such as water, saline, or orange juice; (b) capsules, sachets, tablets, lozenges, and troches, each containing a pre-determined amount of the compound of the invention, as solids or granules; (c) powders; (d) suspensions in an appropriate liquid; and (e) suitable emulsions. Liquid formulations can include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the compound ingredient in a flavor, usually sucrose and acacia or tragacanth, as well as pastilles comprising a compound of the invention in an inert base, such as gelatin and glycerin, or sucrose and acacia, emulsions, gels, and the like containing, in addition to the compound of the invention, such excipients as are known in the art.

An compound or epimer of the present invention, alone or in combination with other suitable components, can be made into aerosol formulations to be administered via inhalation. A compound or epimer of the invention is preferably supplied in finely divided form along with a surfactant and propellant. Typical percentages of the compounds of the invention can be about 0.01% to about 20% by weight, preferably about 1% to about 10% by weight. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides can be employed. The surfactant can constitute from about 0.1% to about 20% by weight of the composition, preferably from about 0.25% to about 5%. The balance of the composition is ordinarily propellant. A carrier can also be included as desired, e.g., lecithin, for intranasal delivery. These aerosol formulations can be placed into acceptable pressurized propellants, such as dichlorodifluoromethane, propane, nitrogen, and the like. They also can be formulated as pharmaceuticals for non-pressured preparations, such as in a nebulizer or an atomizer. Such spray formulations can be used to spray mucosa.

Additionally, the compound or epimer of the invention can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the compound ingredient, such carriers as are known in the art to be appropriate.

The concentration of the compound or epimer in the pharmaceutical formulations can vary, e.g., from less than about 1% to about 10%, to as much as 20% to 50% or more by weight, and can be selected primarily by fluid volumes, and viscosities, in accordance with the particular mode of administration selected.

Thus, a typical pharmaceutical composition for intravenous infusion could be made up to contain 250 ml of sterile Ringer's solution, and 100 mg of at least one compound of the invention. Actual methods for preparing parenterally administrable compounds of the invention will be known or apparent to those skilled in the art and are described in more detail in, for example, *Remington's Pharmaceutical Science* ($17^{th}$ ed., Mack Publishing Company, Easton, Pa., 1985).

It will be appreciated by one of ordinary skill in the art that, in addition to the aforedescribed pharmaceutical compositions, the compound of the invention can be formulated as inclusion complexes, such as cyclodextrin inclusion complexes, or liposomes. Liposomes can serve to target a compound of the invention to a particular tissue, such as lymphoid tissue or cancerous hepatic cells. Liposomes can also be used to increase the half-life of a compound of the invention. Many methods are available for preparing liposomes, as described in, for example, Szoka et al., *Ann. Rev. Biophys. Bioeng.*, 9, 467 (1980) and U.S. Pat. Nos. 4,235,871, 4,501,728, 4,837,028, and 5,019,369.

In accordance with some embodiments, the compound of formula (I) is administered as an adjuvant in combination with an anti-viral agent or combination of agents. For example, in some embodiments, the combinatorial formulation may include one or more compounds from a highly active antiretroviral therapy protocol (HAART protocols) in combination with a compound of formula (I), among other combinations. Other combinatorial formulations may, for example, include a compound of formula (I) and/or compounds effective in treating the opportunistic infections of AIDS as well as compounds from HAART protocols. In other embodiments, the combinatorial formulation may include one or more additional chemotherapeutic agents.

To practice coordinate administration methods of the invention, a compound of formula (I) may be administered, simultaneously or sequentially, in a coordinate treatment protocol with one or more of the secondary or adjunctive therapeutic agents contemplated herein. Thus, in certain embodiments compound of formula (I) is administered coordinately with a different agent, or any other secondary or adjunctive therapeutic agent contemplated herein, using separate formulations or a combinatorial formulation as described above (i.e., comprising both compound of formula (I) or related or derivative compound, and another therapeutic agent). This coordinate administration may be done simultaneously or sequentially in either order, and there may be a time period while only one or both (or all) active therapeutic agents individually and/or collectively exert their biological activities.

In one embodiment, such coordinate treatment methods may, for example, follow or be derived from various highly active antiretroviral therapy protocols (HAART protocols) and include regimens such as, but not limited to, two nucleoside analogue reverse transcriptase inhibitors plus one or more protease inhibitor or non-nucleoside analogue reverse transcriptase inhibitor with a compound of formula (I), among other combinations. Other coordinate treatment methods may, for example, include a compound of formula (I) and/or treatments for opportunistic infections as well as compounds from HAART protocols. A distinguishing aspect of all such coordinate treatment methods is that the compound of formula (I) exerts at least some activity, which yields a favorable clinical response in conjunction with a complementary AIDS symptom decreasing, or distinct, clinical response provided by the secondary or adjunctive therapeutic agent. Often, the coordinate administration of the compound of with the secondary or adjunctive therapeutic agent will yield improved therapeutic or prophylactic results in the subject beyond a therapeutic effect elicited by the compound of formula(I), or the secondary or adjunctive therapeutic agent administered alone. This qualification contemplates both direct effects, as well as indirect effects.

Within exemplary embodiments, a compound of formula (I) will be coordinately administered (simultaneously or sequentially, in combined or separate formulation(s)), with one or more secondary treating agents, or other indicated or adjunctive therapeutic agents, e.g., selected from, for example, protease inhibitors, including, but not limited to, saquinavir, indinavir, ritonavir, nelfinavir, atazanavir, darunavir, fosamprenavir, tipranavir and amprenavir; nucleoside reverse transcriptase inhibitors including but not limited to, zidovudine, didanosine, stavudine, lamivudine, zalcitabine, emtricitabine, tenofovir disoproxil fumarate, AVX754 and abacavir; non-nucleoside reverse transcriptase inhibitors including, but not limited to, nevaripine, delavirdine, calanolide A, TMC125 and efavirenz; combination drugs including, but not limited to, efavirenz/emtricitabine/tenofovir disoproxil fumarate, lamivudine/zidovudine, abacavir/lamivudine, abacavir/lamivudine/zidovudine, emtricitabine/tenofovir disoproxil fumarate, sulfamethoxazole/trimethoprim, and lopinavir/ritonavir; entry and fusion inhibitors, including, but not limited to, enfuvirtide, AMD070, BMS-488043, fozivudine tidoxil, GSK-873,140, PRO 140, PRO 542, Peptide T, SCH-D, TNX-355, and UK-427,857; treatments for opportunistic infections and other conditions associated with AIDS and HIV including, but not limited to, acyclovir, adefovir dipivoxil, aldesleukin, amphotericin b, azithromycin, calcium hydroxylapatite, clarithromycin, doxorubicin, dronabinol, entecavir, epoetin alfa, etoposide, fluconazole, ganciclovir, immunoglobulins, interferon alfa-2, ionomycine, isoniazid, itraconazole, megestrol, paclitaxel, peginterferon alfa-2, pentamidine, poly-1-lactic acid, ribavirin, rifabutin, rifampin, somatropin, testosterone, trimetrexate, and valganciclovir; integrase inhibitors including, but not limited to, GS 9137, MK-0518; microbicides, including, but not limited to, BMS-378806, C31G, carbopol 974P, carrageenan, cellulose sulfate, cyanovirin-N, dextran sulfate, hydroxyethyl cellulose, PRO 2000, SPL7013, tenofovir, and UC-781, and IL-2.

In certain embodiments, the invention provides a kit for therapeutically treating an HTLV-infected animal comprising (a) a compound of formula (I), (b) at least one anti-retroviral agent, and (c) instructions for use. In certain other embodiments, the invention provides a kit for therapeutically treating an HIV-infected animal comprising (a) a compound of formula (I), (b) at least one anti-retroviral agent, and (c) instructions for use.

In these embodiments, an article of manufacture, or "kit", containing materials useful for the treatment of the diseases and disorders described above is provided. In one embodiment, the kit comprises a container comprising a compound of formula (I), a container comprising at least one anti-retroviral agent, or a container comprising a composition comprising a compound of formula (I) and at least one anti-retroviral agent. The kit may further comprise a label or package insert, on or associated with the container(s). The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, and the like. The container(s) may be formed from a variety of materials such as glass or plastic. The container(s) may have a sterile access port (for example, the container may be an intravenous solution bag or a vial having a stopper pierceable by a hypodermic injection needle). At least one active agent in the composition is a compound of formula (I). The label or package insert indicates that the composition is used for treating the condition of choice, such as HIV infection, AIDS, HTLV infection, or adult T cell leukemia/lymphoma. The label or package insert may also indicate that the composition can be used to treat other disorders. Alternatively, or additionally, the article of manufacture may further comprise a second or third container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of formula (I) and a separate composition comprising an anti-retroviral agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

The following examples further illustrate the invention but, of course, should not be construed as in any way limiting its scope.

EXAMPLE 1

This example demonstrates the effect of englerin A on the transcriptional activity of NFκB and HSF1 in 293A cells.

293A cells were transiently transfected with PKCθ or a control plasmid for 24 h prior to transfection with reporter plasmids for either NFκB or HSF1 to measure their transcriptional activity. Simultaneously, cells were treated with 0.1 µM englerin A for 24 h. Transcriptional activity was quantified by luminescence, and the results set forth in Tables 1 and 2.

TABLE 1

NFkB transcriptional activity (%)

|  |  | NFκB Transcriptional Activity (%) |
|---|---|---|
| No PKCθ | Control | 99.99865 |
|  | englerin A | 104.8113 |
| PKCθ | Control | 102.9152 |
|  | englerin A | 120.3657 |

TABLE 2

HSF1 Transcriptional Activity (%)

|  |  | HSF1 Transcriptional Activity (%) |
|---|---|---|
| No PKCθ | Control | 99.99767 |
|  | englerin A | 99.12789 |
| PKCθ | Control | 103.6724 |
|  | englerin A | 130.278 |

As is apparent from the results set forth in Tables 1 and 2, 293A cells not transfected with PKCθ exhibited an approximately 5% increase in NFkB transcriptional activity when treated with englerin A as compared with control. 293A cells transfected with PKCθ exhibited an approximately 17% increase in NFκB transcriptional activity when treated with englerin A as compared with control. 293A cells not transfected with PKCθ exhibited an approximately 1% decrease in HSF1 transcriptional activity when treated with englerin A as compared with control. 293A cells transfected with PKCθ exhibited an approximately 26% increase in HSF1transcriptional activity when treated with englerin A as compared with control.

EXAMPLE 2

Figure 1:
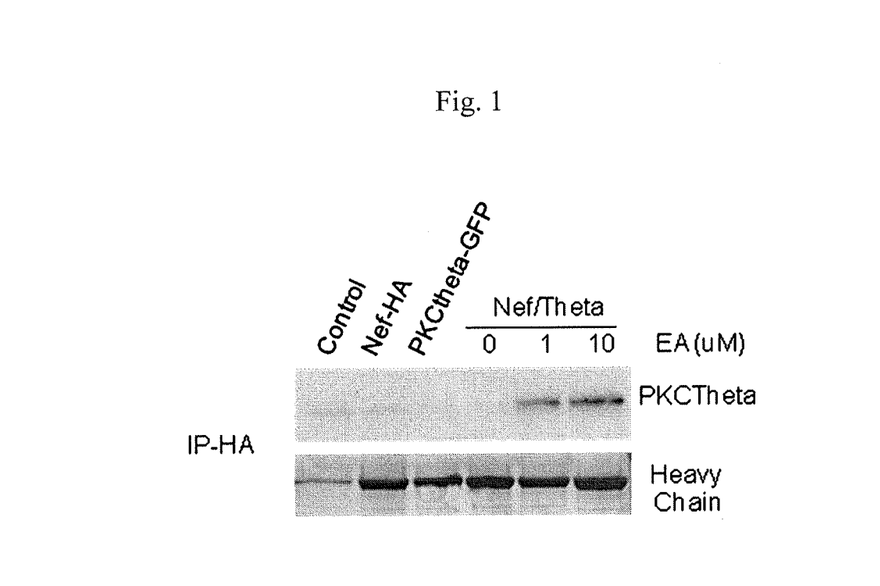
FIG. 1 depicts the effect of englerin A on the association of PKCθ with Nef.

293A cells were transfected with PKCθ for 24 h. The cells were then treated with different concentrations of englerin A (0, 1, and 10 micromoles) for 24 h. 48 h post-transfection and 24 h after treatment with englerin A, Nef protein was immunoprecipitated with antibody for HA. PKCθ (GFP-tagged) association was detected by immunoblotting using antibody for GFP. The results are depicted in FIG. 1, which shows that englerin A causes a dose-dependent interaction of PKCθ with Nef.

EXAMPLE 3

Peripheral blood mononuclear cells (PBMCs) obtained from normal volunteers were activated with antibodies to CD3 and CD28, and were treated with englerin A (1 microM) for 24 h. Expression of Treg markers CD8+ and CD4+ was analyzed by flow cytometry. The results are set forth in Table 2.

TABLE 2

|  | CD4 + Treg | CD8 + Treg |
|---|---|---|
| PBMC | 1 | 1 |
| PBMC + englerin A | 0.69 | 0 |
| PBMC + CD3 + CD28 | 18.5 | 249 |
| PBMC + CD3 + englerin A | 5.44 | 70 |

As is apparent from the results set forth in Table 2, englerin A significantly inhibits Treg activation and number.

EXAMPLE 4

PBMC's from normal volunteers were treated with nothing (control), englerin A, ionomycine, and englerin A and ionomycine. mRNA for IL-4, INF-gamma, TNF-alpha, and CD69 were measured and expressed as the relative fold difference versus untreated control. The results are set forth in Table 3.

TABLE 3

| Control | englerin A | Ionomycine |  |
|---|---|---|---|
| IL-4 | | | |
| | | | Ionomycine + Englerin A |
| 1 | 0.446 | 0.716 | 1.13 |
| | | | Ionomycine + englerin A |
| IFN-γ | | | |
| 1 | 1.092 | 1.608 | 11.015 |
| TNF-α | | | |
| 1 | 1.211 | 0.657 | 1.503 |
| CD69 | | | |
| 1 | 1.147 | 1.639 | 2.679 |

As is apparent from the results set forth in Table 3, treatment of PBMC's with englerin A and ionomycine induces IFN-γ and CD69 gene expression, suggesting that T lymphocytes, especially Th1 lymphocytes, are activated via PKCθ.

EXAMPLE 5

PBMC's from 3 ATL patients were treated with englerin A for 24 h. PBMC's from 2 normal patients were treated with englerin A for 24 h and were used as a control. PBMC's from 3 ATL patients and from 2 normal patients (as a control) were treated with four dosages of englerin A for 24 h (0 μM, 0.3 μM, 1 μM, and 3 μM). The percentage of Treg in CD4+ T cells was determined, and the results set forth in Table 4.

TABLE 4

| englerin A | Normal #1 | Normal #2 | ATL #1 | ALT #2 | ATL #3 |
|---|---|---|---|---|---|
| 0 μM   | 2.75 | 1.57 | 10.2 | 3.85 | 10.5 |
| 0.3 μM | 3.06 | 1.7  | 10.3 | 3.66 | 11.4 |
| 1 μM   | 2.43 | 1.54 | 9.26 | 4.09 | 8.87 |
| 3 μM   | 2.35 | 1.52 | 8.44 | 4.12 | 9.55 |

As is apparent from the results set forth in Table 4, englerin A was able to decrease the population of Treg in the patients' blood samples that displayed a higher number of Treg than normal.

EXAMPLE 6

Figure 2:
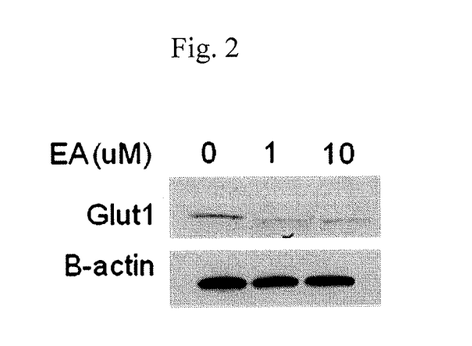
FIG. 2 depicts the decreased expression of Glut1 by 786-0 cells upon treatment with englerin A.

786-0 cells were treated for 30 min with englerin A. After extraction of the whole cell lysate, expression of Glut1 was assessed by immunoblotting. The results are depicted in FIG. 2. As is apparent from FIG. 2, englerin A decreases the expression of Blut1, the receptor responsible for HTLV infection.

The invention includes the following aspects.

1. A method of treating an HIV-infected animal comprising co-administering to the animal (i) an effective amount of a compound of formula (I):

(I)

or an epimer thereof; wherein

Ar is an aryl group, optionally substituted with one or more substituents selected from the group consisting of $C_1$-$C_6$ alkyl, $C_1$-$C_6$ hydroxyalkyl, $C_1$-$C_6$ alkoxy, halo, and nitro;

X is O, NH, or S;

$R^2$ and $R^3$ are independently $C_1$-$C_6$ alkyl;

$R^1$ is isopropyl or isopropenyl;

"a" is a single bond or a double bond;

when "a" is a double bond, $R^4$ is hydrogen, and $R^5$ is halo or H;

when "a" is a single bond, $R^4$ is selected from the group consisting of halo, hydroxy, and $C_1$-$C_6$ alkoxy and $R^5$ is halo or H; and $R^6$ is H, $C_1$-$C_6$ alkyl carbonyl, or hydroxy $C_1$-$C_6$ alkyl carbonyl, and (ii) at least one antiviral agent.

2. A method of treating an HTLV-infected animal comprising co-administering to the animal (i) an effective amount of a compound of formula (I):

(I)

or an epimer thereof; wherein

Ar is an aryl group, optionally substituted with one or more substituents selected from the group consisting of $C_1$-$C_6$ alkyl, $C_1$-$C_6$ hydroxyalkyl, $C_1$-$C_6$ alkoxy, halo, and nitro;

X is O, NH, or S;

$R^2$ and $R^3$ are independently $C_1$-$C_6$ alkyl;

$R^1$ is isopropyl or isopropenyl;

"a" is a single bond or a double bond;

when "a" is a double bond, $R^4$ is hydrogen, and $R^5$ is halo or H;

when "a" is a single bond, $R^4$ is selected from the group consisting of halo, hydroxy, and $C_1$-$C_6$ alkoxy and $R^5$ is halo or H; and $R^6$ is H, $C_1$-$C_6$ alkyl carbonyl, or hydroxy $C_1$-$C_6$ alkyl carbonyl, and (ii) at least one antiviral agent.

3. A method of increasing the activity of latent infected CD4+ cells of an animal carrying HIV comprising administering to the animal an effective amount of a compound of formula (I):

(I)

or an epimer thereof; wherein

Ar is an aryl group, optionally substituted with one or more substituents selected from the group consisting of $C_1$-$C_6$ alkyl, $C_1$-$C_6$ hydroxyalkyl, $C_1$-$C_6$ alkoxy, halo, and nitro;

X is O, NH, or S;

$R^2$ and $R^3$ are independently $C_1$-$C_6$ alkyl;

$R^1$ is isopropyl or isopropenyl;

"a" is a single bond or a double bond;

when "a" is a double bond, $R^4$ is hydrogen, and $R^5$ is halo or H;

when "a" is a single bond, $R^4$ is selected from the group consisting of halo, hydroxy, and $C_1$-$C_6$ alkoxy and $R^5$ is halo or H; and $R^6$ is H, $C_1$-$C_6$ alkyl carbonyl, or hydroxy $C_1$-$C_6$ alkyl carbonyl.

4. A method of inhibiting Treg activation and number in an animal carrying HTLV comprising administering to the animal an effective amount of a compound of formula (I):

(I)

or an epimer thereof; wherein

Ar is an aryl group, optionally substituted with one or more substituents selected from the group consisting of $C_1$-$C_6$ alkyl, $C_1$-$C_6$ hydroxyalkyl, $C_1$-$C_6$ alkoxy, halo, and nitro;

X is O, NH, or S;

$R^2$ and $R^3$ are independently $C_1$-$C_6$ alkyl;

$R^1$ is isopropyl or isopropenyl;

"a" is a single bond or a double bond;

when "a" is a double bond, $R^4$ is hydrogen, and $R^5$ is halo or H;

when "a" is a single bond, $R^4$ is selected from the group consisting of halo, hydroxy, and $C_1$-$C_6$ alkoxy and $R^5$ is halo or H; and $R^6$ is H, $C_1$-$C_6$ alkyl carbonyl, or hydroxy $C_1$-$C_6$ alkyl carbonyl.

5. A method of decreasing Glut1 expression in an ATL cell in an animal carrying HTLV comprising administering to the animal an effective amount of a compound of formula (I):

(I)

or an epimer thereof; wherein

Ar is an aryl group, optionally substituted with one or more substituents selected from the group consisting of $C_1$-$C_6$ alkyl, $C_1$-$C_6$ hydroxyalkyl, $C_1$-$C_6$ alkoxy, halo, and nitro;

X is O, NH, or S;

$R^2$ and $R^3$ are independently $C_1$-$C_6$ alkyl;

$R^1$ is isopropyl or isopropenyl;

"a" is a single bond or a double bond;

when "a" is a double bond, $R^4$ is hydrogen, and $R^5$ is halo or H;

when "a" is a single bond, $R^4$ is selected from the group consisting of halo, hydroxy, and $C_1$-$C_6$ alkoxy and $R^5$ is halo or H; and $R^6$ is H, $C_1$-$C_6$ alkyl carbonyl, or hydroxy $C_1$-$C_6$ alkyl carbonyl.

6. The method of any one of aspects 1-4, wherein the compound of formula (I) is englerin A, which is of the formula:

7. The method of any one of aspects 1-5, wherein $R^6$ is hydroxy $C_1$-$C_6$ alkyl carbonyl.

8. The method of claim 7, wherein $R^6$ is hydroxymethyl carbonyl.

9. The method of any one of aspects 1-5, 7, and 8, wherein $R^5$ is halo.

10. The method of claim 9, wherein $R^5$ is chloro.

11. The method of any one of aspects 1-5 and 7-10, wherein Ar is phenyl, optionally substituted with one or more substituents selected from the group consisting of $C_1$-$C_6$ alkyl, $C_1$-$C_6$ hydroxyalkyl, $C_1$-$C_6$ alkoxy, halo, and nitro.

12. The method of claim 11, wherein Ar is phenyl.

13. The method of any one of aspects 1-5 and 7-12, wherein X is O.

14. The method of any one of aspects 1-5 and 7-13, wherein $R^1$ is isopropyl.

15. The method of any one of aspects 1-5 and 7-14, wherein "a" is a double bond and the double bond is E, Z, or a mixture of E and Z.

16. The method of any one of aspects 1-5 and 7-14, wherein "a" is a single bond.

17. The method of any one of aspects 1-5 and 7-16, wherein $R^4$ is hydroxy, chloro, or ethoxy.

18. The method of any one of aspects 1-5 and 7-17, wherein $R^2$ and $R^3$ are methyl.

19. The method of claim 18, wherein the compound of formula (I) is:

2'-Chloroenglerin A,

2'-Chloro,3'-hydroxydihydroenglerin A (epimer 1, 2, 3, or 4),

2',3'-Dichlorodihydroenglerin A (epimer 1 or 2), or

2'-Chloro,3'-ethoxydihydroenglerin A, wherein the double bond "a" in 2'-Chloroenglerin A can be E, Z, or E/Z.

20. The method of any one of aspects 1-5 and 7-18, wherein $R^6$ is $C_1$-$C_6$ alkyl carbonyl.

21. The method of any one of aspects 1-20, wherein the animal is a human.

22. The method of any one of aspects 1-20, wherein the method further comprises administering a highly active antiretroviral therapy regimen to the animal.

23. The method of any one of aspects 1-20, wherein the method further comprises administering at least one antiviral agent to the animal.

24. The method of any one of aspects 1-20, wherein the method results in an induction of NFκB transcriptional activity in the animal.

25. The method of any one of aspects 1-20, wherein the method results in an induction of HSF1 transcriptional activity in the animal.

26. The method of any one of aspects 1-20, wherein the animal is afflicted with an ailment selected from HIV1 infection, AIDS, HTLV infection, and adult T cell leukemia/lymphoma.

27. A pharmaceutical composition comprising a compound of formula (I) and at least one anti-retroviral agent.

28. The pharmaceutical composition of claim 27, wherein the compound of formula (I) is englerin A.

29. A kit for therapeutically treating an HTLV-infected animal comprising (a) a compound of formula (I), (b) at least one anti-retroviral agent, and (c) instructions for use.

30. A kit for therapeutically treating an HIV-infected animal comprising (a) a compound of formula (I), (b) at least one anti-retroviral agent, and (c) instructions for use.

31. A compound of formula (I):

or an epimer thereof; wherein

Ar is an aryl group, optionally substituted with one or more substituents selected from the group consisting of $C_1$-$C_6$ alkyl, $C_1$-$C_6$ hydroxyalkyl, $C_1$-$C_6$ alkoxy, halo, and nitro;

X is O, NH, or S;

$R^2$ and $R^3$ are independently $C_1$-$C_6$ alkyl;

$R^1$ is isopropyl or isopropenyl;

"a" is a single bond or a double bond;

when "a" is a double bond, $R^4$ is hydrogen, and $R^5$ is halo or H;

when "a" is a single bond, $R^4$ is selected from the group consisting of halo, hydroxy, and $C_1$-$C_6$ alkoxy and $R^5$ is halo or H; and $R^6$ is H, $C_1$-$C_6$ alkyl carbonyl, or hydroxy $C_1$-$C_6$ alkyl carbonyl, or an epimer thereof for use in treating an HIV-infected animal.

32. A compound of formula (I):

or an epimer thereof; wherein

Ar is an aryl group, optionally substituted with one or more substituents selected from the group consisting of $C_1$-$C_6$ alkyl, $C_1$-$C_6$ hydroxyalkyl, $C_1$-$C_6$ alkoxy, halo, and nitro;

X is O, NH, or S;

$R^2$ and $R^3$ are independently $C_1$-$C_6$ alkyl;

$R^1$ is isopropyl or isopropenyl;

"a" is a single bond or a double bond;

when "a" is a double bond, $R^4$ is hydrogen, and $R^5$ is halo or H;

when "a" is a single bond, $R^4$ is selected from the group consisting of halo, hydroxy, and $C_1$-$C_6$ alkoxy and $R^5$ is halo or H; and $R^6$ is H, $C_1$-$C_6$ alkyl carbonyl, or hydroxy $C_1$-$C_6$ alkyl carbonyl, or an epimer thereof for use in treating an HTLV-infected animal.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating an HIV-infected animal or an HTLV-infected animal, increasing the activity of latent infected CD4+ cells of an animal carrying HIV, in inhibiting Treg activation and number in an animal carrying HTLV, and/or in decreasing Glut1 expression in an ATL cell in an animal carrying HTLV, comprising administering to the animal a compound of formula (I):

(I)

or an epimer thereof; wherein
Ar is an aryl group, optionally substituted with one or more substituents selected from the group consisting of $C_1$-$C_6$ alkyl, $C_1$-$C_6$ hydroxyalkyl, $C_1$-$C_6$ alkoxy, halo, and nitro;
X is O, NH, or S;
$R^2$ and $R^3$ are independently $C_1$-$C_6$ alkyl;
$R^1$ is isopropyl or isopropenyl;
"a" is a single bond or a double bond;
when "a" is a double bond, $R^4$ is hydrogen, and $R^5$ is halo or H;
when "a" is a single bond, $R^4$ is selected from the group consisting of halo, hydroxy, and $C_1$-$C_6$ alkoxy and $R^5$ is halo or H; and
$R^6$ is H, $C_1$-$C_6$ alkyl carbonyl, or hydroxy $C_1$-$C_6$ alkyl carbonyl,
and at least one antiviral agent.

2. The method according to claim 1, wherein the compound of formula (I) is englerin A, which is of the formula:

3. The method according to claim 1, wherein $R^6$ is hydroxy $C_1$-$C_6$ alkyl carbonyl or hydroxymethyl carbonyl.

4. The method according to claim 1, wherein $R^5$ is halo.

5. The method according to claim 4, wherein $R^5$ is chloro.

6. The method according to claim 1, wherein Ar is phenyl, optionally substituted with one or more substituents selected from the group consisting of $C_1$-$C_6$ alkyl, $C_1$-$C_6$ hydroxyalkyl, $C_1$-$C_6$ alkoxy, halo, and nitro.

7. The method according to claim 1, wherein X is O.

8. The method according to claim 1, wherein $R^1$ is isopropyl.

9. The method according to claim 1, wherein "a" is a double bond and the double bond is E, Z, or a mixture of E and Z.

10. The method according to claim 1, wherein "a" is a single bond.

11. The method according to claim 1, wherein $R^4$ is hydroxy, chloro, or ethoxy.

12. The method according to claim 1, wherein $R^2$ and $R^3$ are methyl.

13. The method according to claim 12, wherein the compound of formula (I) is:

2'-Chloroenglerin A,

2'-Chloro, 3'-hydroxydihydroenglerin A (epimer 1, 2, 3, or 4),

2',3'-Dichlorodihydroenglerin A (epimer 1 or 2), or

2'-Chloro, 3'-ethoxydihydroenglerin A, wherein the double bond "a" in 2'-Chloroenglerin A is E, Z, or E/Z.

14. The method according to claim 1, wherein the animal is a human.

15. The method according to claim 1, which is in further combination with a highly active antiretroviral therapy regimen to the animal.

16. The method according to claim 1, which results in an induction of NFκB transcriptional activity or an induction of HSF1 transcriptional activity in the animal.

17. The method according to claim 1, wherein the animal is afflicted with an ailment selected from HIV1 infection, AIDS, HTLV infection, and adult T cell leukemia/lymphoma.

18. A pharmaceutical composition comprising a compound of formula (I):

(I)

or an epimer thereof; wherein

Ar is an aryl group, optionally substituted with one or more substituents selected from the group consisting of $C_1$-$C_6$ alkyl, $C_1$-$C_6$ hydroxyalkyl, $C_1$-$C_6$ alkoxy, halo, and nitro;

X is O, NH, or S;

$R^2$ and $R^3$ are independently $C_1$-$C_6$ alkyl;

$R^1$ is isopropyl or isopropenyl;

"a" is a single bond or a double bond;
when "a" is a double bond, $R^4$ is hydrogen, and $R^5$ is halo or H;
when "a" is a single bond, $R^4$ is selected from the group consisting of halo, hydroxy, and $C_1$-$C_6$ alkoxy and $R^5$ is halo or H; and $R^6$ is H, $C_1$-$C_6$ alkyl carbonyl, or hydroxy $C_1$-$C_6$ alkyl carbonyl, and at least one anti-retroviral agent.

19. The pharmaceutical composition of claim 18, wherein the compound of formula (I) is englerin A.

20. A kit for therapeutically treating an HIV-infected animal or an HTLV-infected animal comprising (a) a compound of formula (I), (I)

or an epimer thereof; wherein

Ar is an aryl group, optionally substituted with one or more substituents selected from the group consisting of $C_1$-$C_6$ alkyl, $C_1$-$C_6$ hydroxyalkyl, $C_1$-$C_6$ alkoxy, halo, and nitro;

X is O, NH, or S;

$R^2$ and $R^3$ are independently $C_1$-$C_6$ alkyl;

$R^1$ is isopropyl or isopropenyl;

"a" is a single bond or a double bond;
when "a" is a double bond, $R^4$ is hydrogen, and $R^5$ is halo or H;
when "a" is a single bond, $R^4$ is selected from the group consisting of halo, hydroxy, and $C_1$-$C_6$ alkoxy and $R^5$ is halo or H; and $R^6$ is H, $C_1$-$C_6$ alkyl carbonyl, or hydroxy $C_1$-$C_6$ alkyl carbonyl, (b) at least one anti-retroviral agent, and (c) instructions for use.

* * * * *